(12) United States Patent
Boussand et al.

(10) Patent No.: US 8,058,487 B2
(45) Date of Patent: Nov. 15, 2011

(54) PROCESS FOR THE MANUFACTURE OF PENTAFLUOROETHANE

(75) Inventors: Beatrice Boussand, Sainte Foy les Lyons (FR); Michel Devic, Sainte Foy les Lyons (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 11/606,753

(22) Filed: Nov. 30, 2006

(65) Prior Publication Data

US 2007/0129581 A1   Jun. 7, 2007

(30) Foreign Application Priority Data

Dec. 6, 2005   (FR) ..................... 05 12338

(51) Int. Cl.
*C07C 17/08*   (2006.01)
(52) U.S. Cl. ........ 570/168; 570/161; 570/164; 570/165; 570/169

(58) Field of Classification Search ............. 570/161, 570/164–169
See application file for complete search history.

(56) References Cited

U.S. PATENT DOCUMENTS

| 5,300,711 | A | * | 4/1994 | Corbin et al. | ............... 570/168 |
| 5,545,778 | A | * | 8/1996 | Tung et al. | .................. 570/178 |
| 5,962,753 | A | * | 10/1999 | Shields et al. | ............... 570/169 |
| 6,011,185 | A | | 1/2000 | Yoshimura et al. | |
| 6,049,016 | A | | 4/2000 | Yoshimura et al. | |
| 6,433,233 | B1 | | 8/2002 | Kanemura et al. | |
| 6,503,865 | B1 | | 1/2003 | Kanemura et al. | |
| 7,074,973 | B2 | | 7/2006 | Nappa et al. | |

* cited by examiner

*Primary Examiner* — Sudhakar Katakam
(74) *Attorney, Agent, or Firm* — Steven D. Boyd

(57) ABSTRACT

The present invention relates to a continuous process for the fluorination of perchloroethylene (PER) in the gas phase in a single stage with hydrofluoric acid (HF) in the presence of a catalyst to give, as major product, pentafluoroethane. The process is characterized in that it is carried out at a temperature of between 280 and 430° C. and with an HF/PER molar ratio of greater than or equal to 20.

9 Claims, No Drawings

PROCESS FOR THE MANUFACTURE OF PENTAFLUOROETHANE

FIELD OF THE INVENTION

The present invention relates to a continuous process for the fluorination of perchloroethylene (PER) and has more particularly as subject-matter the fluorination of perchloroethylene in the gas phase with hydrofluoric acid (HF) in the presence of a catalyst to give pentafluoroethane as the major product.

BACKGROUND OF THE INVENTION

The reaction for the fluorination of perchloroethylene with HF in the gas phase in the presence of a catalyst is known. It generally results in the formation of 2,2-dichloro-1,1,1-trifluoroethane (123), 2-chloro-1,1,1,2-tetrafluoroethane (124) and pentafluoroethane (125) with 123 as the major product.

These compounds (denoted overall hereinbelow by the expression ("120 series") can be used either as substitutes for chlorofluorocarbons (CFCs), in the fields of foams (blowing agents and insulators), aerosols (propellants) or refrigeration, or as intermediates in the synthesis of these substitutes. A search is currently underway for high performance processes for the industrial production of pentafluoroethane.

The document WO 92/16479 discloses a process for the manufacture of 2,2-dichloro-1,1,1-trifluoroethane (123), 2-chloro-1,1,1,2-tetrafluoroethane (124) and pentafluoroethane (125) by reacting perchloroethylene (PER) with HF in the gas phase in the presence of a catalyst comprising zinc fluoride supported on fluorinated alumina at a temperature of between 250 and 450° C. and with a contact time of between 0.1 and 60 sec. This document teaches the use preferably of an HF/PER molar ratio of between 3 and 10.

It is recommended, in order to obtain pentafluoroethane as the major product, to carry out the operation in two stages. Thus, the document EP 811 592 provides a two-stage process according to which PER is reacted with HF in the liquid phase in the presence of a catalyst and at a temperature of between 60 and 150° C., to give 123 and/or 1,1,2-trichloro-2,2-difluoroethane (122), and the 123 and/or 122 formed in the first stage is/are subsequently reacted in the vapour phase with HF in the presence of a catalyst and at a temperature of between 250 and 450° C.

Furthermore, this document teaches that, as the reaction for the fluorination of perchloroethylene to give pentafluoroethane is a highly exothermic reaction (28 kcal/mol), there are a number of problems posed by carrying it out in a single stage: the reaction is difficult to control, the catalyst decomposes and significant amounts of by-products are formed.

DETAILED DESCRIPTION OF THE INVENTION

The inventors have discovered a continuous process for the manufacture of pentafluoroethane in a single stage by reacting perchloroethylene with HF in the gas phase which does not exhibit the abovementioned disadvantages.

The present invention thus provides a process for the manufacture of pentafluoroethane in a single stage by reacting perchloroethylene with HF in the gas phase in the presence of a catalyst, characterized in that the process is carried out at a temperature of between 280 and 430° C. and with an HF/PER molar ratio of greater than or equal to 20.

The process according to the present invention is preferably carried out at a temperature of between 300 and 400° C. and advantageously of between 340 and 370° C.

The HF/PER molar ratio is preferably between 20 and 60 and advantageously between 20 and 30.

According to a preferred form of the invention, the HF/PER molar ratio represents a number greater than 20 and less than or equal to 60.

According to a particularly preferred form of the invention, the HF/PER molar ratio represents a number greater than 20 and less than or equal to 30.

Surprisingly, the inventors have observed that, starting from an HF/PER molar ratio of 20, the HF flow rate at the inlet of the reactor per unit of 125 produced begins to decrease. The inventors have also observed that the HF flow rate at the inlet of the reactor per unit of 125 produced is optimal within the preferred range of HF/PER molar ratio. In addition, they have observed that, within the preferred range of HF/PER molar ratio, the amount of 125 produced per unit of catalyst involved is also optimal.

In the process according to the present invention, the contact time, calculated as being the time for the gases (under the reaction conditions) to pass through the volume of catalyst, is between 2 and 50 sec, preferably between 3 and 25 sec.

The process can be carried out at a pressure of less than or equal to 5 bar absolute.

Preferably, the process is carried out at a pressure of between 1 and 3 bar absolute.

Any fluorination catalyst may be suitable for the process of the present invention. The catalyst used preferably comprises oxides, halides, oxyhalides or inorganic salts of chromium, aluminium, cobalt, manganese, nickel, iron or zinc and can be supported. Mention may be made, as support, by way of examples, of alumina, aluminium fluoride or aluminium oxyfluoride.

Use is preferably made of a catalyst based on chromium oxide ($Cr_2O_3$) optionally including another metal at an oxidation state of greater than zero selected from Ni, Co, Mn and Zn. Advantageously, this catalyst can be supported on alumina, aluminium fluoride or aluminium oxyfluoride.

A mixed catalyst composed of oxides, halides and/or oxyhalides of nickel and chromium deposited on a support composed of aluminium fluoride or of a mixture of aluminium fluoride and alumina is very particularly suitable for the process of the present invention.

This catalyst can be prepared in a way known per se starting from an activated alumina. The latter can, in a first stage, be converted to aluminium fluoride or to a mixture of aluminium fluoride and alumina by fluorination using hydrofluoric acid in the presence optionally of air or of an inert gas, such as nitrogen, at a temperature generally of between 200 and 450° C., preferably between 250 and 400° C. The support is subsequently impregnated using aqueous solutions of chromium and nickel salts or using aqueous solutions of chromic acid, of nickel salt and of a reducing agent for chromium, such as methanol.

When chromic acid ($CrO_3$) is used as precursor of the chromium, this chromium can be reduced by any means known to a person skilled in the art, provided that the technique used is not harmful to the properties of the catalyst and thus to its activity. The preferred reducing agent is methanol.

It is preferable, as chromium and nickel salts, to use the chlorides but it is also possible to employ other salts, such as, for example, the oxalates, formates, acetates, nitrates and sulphates, or nickel dichromate, provided that these salts are soluble in the amount of water capable of being absorbed by the support.

The mixed catalyst used in the process according to the invention can also be prepared by direct impregnation of the alumina with the abovementioned solutions of the chromium and nickel compounds. In this case, the conversion of at least a portion of the alumina to aluminium fluoride is carried out during the stage of activation of the catalyst.

The activated aluminas to be used for the preparation of the mixed catalysts are well known products which are available commercially. They are generally prepared by calcination of alumina hydrates at a temperature of between 300 and 800° C. The activated aluminas which can be used in the context of the present invention can comprise high contents (up to 100 ppm) of sodium without this being harmful to the catalytic activity.

The mixed catalyst can comprise, by weight, from 0.5 to 20% of chromium and from 0.5 to 20% of nickel and preferably between 2 and 10% of each of the metals in a nickel/chromium atomic ratio of between 0.5 and 5, preferably in the region of 1.

Before use in the reaction for the fluorination of perchloroethylene, the catalytic solid is subjected beforehand to an activation operation.

This treatment, carried out either "in situ" (in the fluorination reactor) or in suitable equipment, generally comprises the following stages:

low-temperature drying in the presence of air or nitrogen, high-temperature (250 to 450° C., preferably 300 to 350° C.) drying under nitrogen or under air, low-temperature (180 to 350° C.) fluorination using a mixture of hydrofluoric acid and nitrogen, the HF content being controlled so that the temperature does not exceed 350° C., and finishing under a stream of pure hydrofluoric acid or hydrofluoric acid diluted with nitrogen at a temperature which can range up to 450° C.

According to an alternative form of the process, the reaction products after separation of the 125 can be recycled.

The process according to the present invention has the advantage of increasing the proportion of highly fluorinated products (124, 125) in the mixture at the outlet of the reactor, which, in recycling mode, makes it possible to reduce the amount of underfluorinated products to be recycled, some of these products being the cause of deactivation of the catalyst by coking.

Although this is not necessary for the fluorination reaction, it may be judicious to introduce oxygen, at a low content, with the reactants. This content can vary, depending on the operating conditions, between 0.02 and 1 mol %, with respect to the gas mixture entering the reactor.

The process according to the present invention can be carried out in a reactor constructed from corrosion-resistant materials, for example Hastelloy, Inconel and Monel. Any type of reactor may be suitable: for example, multitubular reactor or adiabatic reactor.

Experimental Part

Preparation of the Catalyst 343 g of a support obtained in a preceding stage by fluorination of alumina, Grace HSA, in a stationary bed at approximately 280° C. using air and hydrofluoric acid (concentration by volume of 5 to 10% of this acid in air) was placed in a rotary evaporator. The starting Grace HSA alumina exhibited the following physicochemical characteristics:

form: beads with a diameter of 0.5-2 mm

BET specific surface: 220 m$^2$/g pore volume: 1.3 cm$^3$/g

Furthermore, two separate aqueous solutions are prepared:

| (a) chromic solution with the addition of nickel chloride, comprising: | |
|---|---|
| chromic anhydride | 55 g |
| nickel chloride hexahydrate | 130 g |
| water | 63 g |
| (b) Methanolic solution comprising: | |
| methanol | 81 g |
| water | 8 g |

These two solutions were introduced simultaneously onto the stirred support at a temperature of 40° C. at atmospheric pressure over approximately 2 hours. After a stage of maturing under nitrogen, the catalyst was dried under nitrogen, then under vacuum at 65° C. and then at approximately 90° C. for 6 hours.

500 g of impregnated solid were charged to a tubular reactor made of Inconel. The catalyst was first dried while flushing with nitrogen at low temperature and then up to 320° C., at atmospheric pressure. It is subsequently fluorinated in the presence of a hydrofluoric acid/nitrogen mixture (concentration by volume of 5 to 10% of this acid in nitrogen) at 320° C. and then up to 390° C. The HF feed was then cut off. Flushing with nitrogen was maintained for 15 minutes at 390° C. and then the catalyst was cooled down to 60° C. while flushing with nitrogen.

The examples below were carried out using a pilot unit for continuous gas phase fluorination. This pilot unit comprises a reactor composed of a tube made of Inconel with an internal diameter of 22.5 mm and a length of 500 mm placed vertically in a tubular electric oven. A ⅛th of an inch (3.175 mm) Inconel sleeve is placed coaxially at the centre of the tube and a movable thermocouple makes it possible to plot the temperature profile along the reactor.

The catalytic bed was composed of a lower layer of corundum with a thickness of 180 mm, then of a layer of catalyst with a thickness of 120 mm (volume: 48 cm$^3$, weight: 42.9 g) and of an upper layer of corundum with a thickness of 60 mm.

The catalyst was first dried at atmospheric pressure and then it was activated by passing an HF flow of 0.286 mol/h at 355° C. for 24 h. A flow of nitrogen of 12 l/h was added during the first hour of the activation of the catalyst.

The reactants are subsequently introduced continuously at the upper end of the reactor and preheated to the temperature of the oven through the upper layer of corundum, the gaseous reaction products exit at the lower end of the reactor through a pressure control valve and the gas stream exiting from the valve was analysed by gas chromatography.

The characteristics of the catalyst after activation were as follows:

| BET specific surface: | 40 m$^2$/g |
|---|---|
| pore volume: | 0.4 cm$^3$/g |
| chemical composition by weight: | |
| Al: | 25% |
| F: | 58% |
| Cr: | 5.3% |
| Ni: | 6.4% |

The same amount of 42.9 g was used for all the tests in Table 1.

|  | Ex. 1 | Ex. 2 | Ex. 3 | Ex. 4 | Ex. 5 | Ex. 6 | Ex. 7 |
|---|---|---|---|---|---|---|---|
| Temperature (maximum) of the hot spot of the catalyst (° C.) | 359 | 358 | 358 | 359 | 360 | 360 | 360 |
| HF/PER molar ratio | 10 | 20 | 25 | 30 | 25 | 26 | 45 |
| HF flow rate at the inlet of the reactor (mmol/h) | 630 | 1014 | 658 | 528 | 617 | 640 | 652 |
| PER flow rate at the inlet of the reactor (mmol/h) | 62.9 | 50.9 | 26.32 | 17.8 | 24.14 | 24.25+ 9.52 (124) | 14.39+ 6.45 (124) + 1.34 (123) |
| Pressure at the inlet of the reactor (bar absolute) | 1 | 1 | 1 | 1 | 2 | 2 | 2 |
| DC PER % | 63.3 | 70.9 | 88.7 | 93.5 | 97.9 | 99 | 100 |
| Composition of the organic mixture at the outlet of the reactor (mol %) | | | | | | | |
| 125 | 19.2 | 33.2 | 50.5 | 62 | 47.1 | 68 | 70 |
| 124 | 36.5 | 34.7 | 29.2 | 23.7 | 32.3 | 21.8 | 19.4 |
| 123 | 29.6 | 20.6 | 12.6 | 8.3 | 12.5 | 5.76 | 4.8 |
| Flow rate of 125 at the outlet of the reactor (mmol/h) | 7.65 | 11.96 | 11.8 | 10.32 | 11.37 | 22.95 | 15.52 |
| Productive output of 125 in g/h/l of catalyst | 19.1 | 29.9 | 29.5 | 25.8 | 28.4 | 57.3 | 38.8 |
| HF stream (kg) at the inlet of the reactor per kg of 125 produced | 13.73 | 14.13 | 9.27 | 8.53 | 9.04 | 4.65 | 7.0 |

DC: degree of conversion.

The invention claimed is:

1. Process for the manufacture of pentafluoroethane in a single stage comprising reacting perchloroethylene with hydrofluoric acid in the gas phase in the presence of a catalyst, characterized in that the process is carried out at a temperature of between 300 and 400° C. and with an hydrofluoric acid/perchloroethylene molar ratio of 25 or greater and equal to or less than 30 wherein the process is carried out at a pressure less than 3 bar absolute.

2. Process according to claim 1, characterized in that the temperature is between 340 and 370° C.

3. Process according to claim 1, characterized in that the process is carried out at a pressure of between 1 and 3 bar absolute.

4. Process according to claim 1, characterized in that the catalyst is selected from oxides, halides, oxyhalides or inorganic salts of chromium, aluminium, cobalt, manganese, nickel, iron or zinc.

5. Process according claim 1, characterized in that the catalyst is based on chromium oxide ($Cr_2O_3$).

6. Process according to claim 5, characterized in that said catalyst further includes a metal at an oxidation state of greater than zero selected from Ni, Co, Mn or Zn.

7. Process according to claim 1, characterized in that the catalyst is composed of oxides, halides and/or oxyhalides of nickel and chromium.

8. Process according to claim 1, characterized in that the catalyst is supported.

9. Process according to claim 8, characterized in that the catalyst is supported on alumina, aluminium fluoride or aluminium oxyfluoride.

* * * * *